United States Patent
Klein

(10) Patent No.: US 11,862,304 B1
(45) Date of Patent: Jan. 2, 2024

(54) PATIENT AUTHORIZED MEDICAL INFORMATION STORAGE AND ACCESS SYSTEM

(71) Applicant: Health2047, Inc., Menlo Park, CA (US)

(72) Inventor: Justin James Klein, Mountain View, CA (US)

(73) Assignee: Health2047, Inc., Menlo Park, CA (US)

( * ) Notice: Subject to any disclaimer, the term of this patent is extended or adjusted under 35 U.S.C. 154(b) by 22 days.

(21) Appl. No.: 16/413,456

(22) Filed: May 15, 2019

Related U.S. Application Data

(60) Provisional application No. 62/671,974, filed on May 15, 2018.

(51) Int. Cl.
| | | |
|---|---|---|
| *G16H 10/40* | (2018.01) | |
| *G16H 10/60* | (2018.01) | |
| *G06F 21/62* | (2013.01) | |
| *H04L 9/40* | (2022.01) | |

(52) U.S. Cl.
CPC ......... *G16H 10/60* (2018.01); *G06F 21/6245* (2013.01); *G16H 10/40* (2018.01); *H04L 63/04* (2013.01)

(58) Field of Classification Search
CPC .... G16H 10/60; G16H 10/40; G06F 21/6245; H04L 63/04
See application file for complete search history.

(56) References Cited

U.S. PATENT DOCUMENTS

| | | | |
|---|---|---|---|
| 9,641,332 B1 * | 5/2017 | Yung | H04L 9/30 |
| 2009/0070146 A1 * | 3/2009 | Haider | G16H 10/60 |
| | | | 705/3 |
| 2011/0145216 A1 * | 6/2011 | Subramanya | G06F 16/1734 |
| | | | 707/694 |
| 2018/0082024 A1 * | 3/2018 | Curbera | G16H 40/63 |
| 2018/0117447 A1 * | 5/2018 | Tran | G06Q 20/382 |
| 2018/0191503 A1 * | 7/2018 | Alwar | H04L 9/14 |
| 2018/0196694 A1 * | 7/2018 | Banerjee | G06F 9/466 |

* cited by examiner

*Primary Examiner* — Jason S Tiedeman
*Assistant Examiner* — Liza Tony Kanaan
(74) *Attorney, Agent, or Firm* — Knobbe, Martens, Olson & Bear, LLP

(57) ABSTRACT

Systems and methods for a patient authorized medical information storage and access system. One of the methods includes receiving information indicating a transaction is to be performed between two entities, the transaction indicating an event associated with transfer or receipt of medical information; accessing a patient master index to confirm that the two entities are authorized to transfer or receive the medical information; causing generation of a blockchain transaction between the two entities; updating the patient master index to reflect the transaction; and enabling access, by a receiving entity of the two entities, to the medical information.

21 Claims, 8 Drawing Sheets

US 11,862,304 B1

PATIENT AUTHORIZED MEDICAL INFORMATION STORAGE AND ACCESS SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present disclosure relates to systems and techniques for security, data integration, and visualization. More specifically, this disclosure relates to secure identification of computing systems and authorizing actions based on transference of secure information.

BACKGROUND

Patient health records are invaluable in determining a patient's current health state and future health risk indicators. Medical information and associated health records, however, are generated using complex disparate proprietary systems and stored in different locations making it difficult to access and compile. Existing systems also often provide inconsistent access to stored medical information. For example, a hospital may have many different proprietary computer systems that each separately record and maintain medical information of patients in unique proprietary formats. A medical professional can access the medical information, but only on specific computer systems in specific wards of the hospital. This often results in requests for hard copies of medical information pulled one at a time from various storage systems by a variety of personnel, causing significant wait times.

Complicating access to medical information, a patient may desire to view all medical information associated with him/her. For example, the patient may desire access to an x-ray image taken of the patient. To obtain access, a patient may be required to travel to a hospital to view the x-ray or wait for a version sent in the mail to the patient. Additionally, if the patient prefers visiting a second hospital the patient may have trouble having the x-ray transferred to the second hospital. Furthermore, the patient may have difficult restricting access to his/her medical information by different medical professionals. The patient may therefore have to rely on verbally providing such access restrictions, for example when ceasing work with a first medical professional to work with a second medical professional.

SUMMARY

Particular embodiments of the subject matter described in this specification can be implemented so as to realize one or more of the following advantages. Medical information associated with a patient may be controlled by the patient, and access rights to the medical information tightly constrained. For example, the patient may utilize an application executing on his/her user device to specify access rights for portions of the medical information. As will be described, the application may access a patient master index that defines access rights afforded by the patient to different parties. As an example, the patient can update the patient master index to indicate that medical information can be shared with a first hospital. As another example, the patient can update the patient master index to indicate that medical information can be shared with a particular medical professional at the first hospital. In this example, the particular medical professional may utilize a device to request medical information of the patient. When requesting the medical information, the device may access the patient master index to confirm that the particular medical professional is authorized.

Additionally, a first medical professional authorized to access a patient's medical information may cause transfer of the patient's medical information to a second medical professional. The patient master index may be accessed to confirm that the first medical professional is authorized to transfer the patient's medical information. Optionally, the patient master index may be accessed to confirm that the second medical professional is authorized to receive the patient's medical information. The patient master index may then be updated to reflect the transfer. Thus, the patient master index may specify access rights to a patient's medical information. The patient master index may further specify all authorized transactions (e.g., transfer of medical information) involving the patient's medical information.

Additionally, the technical scheme described herein can advantageously enable duplication of patients' medical information at different locations without any loss of security. For example, instead of storing medical information at a particular hospital, the medical information may be spread around different storage systems located at different hospitals or secured offsite systems. In this way, the particular hospital's storage burden may be reduced. To ensure security, the medical information may optionally be stored according to a content-addressable file system. An example content-addressable file system includes the interplanetary file system (IPFS), which enables access to information based on complex unique hash values associated with stored information. IPFS further enables versioning of information, such that specific slices or sheets at a point in time may be provided, and ensure that stored information is unable to be tampered or modified with. As will be described, access to medical information may be provided as access to particular unique hash values corresponding to stored medical information. IPFS, such as specific IPFS nodes, may additionally balance locations at which medical information is stored. In this way, a patient located in a geographic region may have his/her medical information stored in the same geographic region. Since medical information is stored at multiple locations (e.g., IPFS nodes), loss of data from one or more locations may be recoverable from other locations. Latency of access to medical information may additionally be reduced (e.g., as compared to a cloud-based storage systems), as medical information of the patient may be provided directly from the IPFS nodes in the geographic location.

As will be described, to ensure that access to medical information is tightly restricted, a blockchain network may be utilized. Example blockchain networks may include Ethereum, Hyperledger, Skyledger, and so on. It should be appreciated that these example blockchain networks are not to be considered exhaustive. Additionally, other distributed ledger techniques may be employed and fall within the present disclosure. As an example, a patient may be associated with a patient identifying blockchain address. To share medical information with a third party, the patient may cause a transaction to be placed on the blockchain network. The blockchain transaction can indicate a sending address and a receiving address. To mask the patient's identity, the sending address may be unique to the particular transaction.

For example, the sending address may be a unique transaction address specific for that transaction. As described above, the patient may be associated with a patient identifying address. Each unique transaction address may be recorded, for example in a file or other information, and this recorded information may be encrypted utilizing a private key associated with the patient identifying address. In this way, the patient may utilize his/her private key to obtain all unique transaction keys. Thus, the patient can identify all transactions that utilize the patient's medical information. The receiving address may be a blockchain address associated with the third party. Therefore, the blockchain transaction described above can indicate a unique transaction address and the blockchain address associated with the third party.

With respect to the blockchain transaction described above, the transaction can further specify an event that is associated with the transfer of medical information. An example event may include a digital request for medical information. For example, a patient may request access to his/her medical information from a medical professional. As another example, a medical professional may request access to a patient's medical information from the patient or from another medical professional. Another example event may include a medical event, such as the patient visiting a medical professional.

As will be described in more detail, the specified event may be recorded in the patient master index described above. In addition, the specified event may include, or be associated with, encrypted information indicating medical information to be shared with the third party. To decrypt this information, the third party can utilize a private key associated with their blockchain address and optionally a private key associated with the unique transaction address. For example, the private key may be provided to them via an oracle or other secure software. In this example, a smart contract may be used to cause the private key to be provided. It will be appreciated that an oracle may represent a trusted data feed which can provide information to a smart contract, receive information from a smart contract, and so on. As an example, an oracle may take real world data for smart contracts to act on. Optionally, a smart contract may cause the receiving entity to be authenticated. The smart contract may then cause decryption of the event and may cause routing of the decrypted information to the third party. In this way, the third party may obtain information indicating the shared medical information. In accordance with the content addressable file system described above, the obtained information may include unique hash values of the medical information. The patient master index may further reflect that the third party is authorized to access the specific shared medical information. This authorization may further indicate whether the third party is authorized to share the medical information with other parties, whether they have read and/or write privileges, and so on.

In this way, the patient master index may represent a summary of all transactions involving a patient's medical information. Additionally, the patient master index may be utilized as a front-end into the patient controlling his/her medical information. Thus, in contrast to prior schemes, the patient is at the forefront of control of his/her medical information. As will be described, the patient may view a representation of the patient master index, for example on his/her mobile device, and may perform actions with respect to his/her medical information. For example, the patient may specify access rights to his/her medical information. As another example, the patient may view information identifying some, or all of, their medical information (e.g., specific patient health records, images, and so on). The patient may then select some, or all, of the identified information, and may cause the selected information to be shared with third parties.

The patient master index may therefore be relied upon to control access to medical information, and thus enable ownership of medical information by a patient. Advantageously, the patient master index may be encrypted according to one or more schemes. For example, the patient master index may be decrypted by the patient using a private key associated with his/her patient identity address. Additionally, the patient master index may be partially decrypted using a private key associated with a unique transaction address. Optionally, the patient master index may be partially decrypted using a private key associated with any third party authorized to view medical information of the patient. As an example, a third party may utilize their private key to decrypt specific information in the patient master index, such as events for which they are a party. Optionally, to further decrypt an event (e.g., to obtain hash values corresponding to medical information as described above), the third party may be required to utilize a private key associated with a transaction involving the event.

Since the patient master index may be encrypted at several different levels, with private keys safeguarded by the blockchain network, the patient master index may be mirrored in different storage locations. For example, the patient master index may be stored on a patient's mobile device. As another example, the patient master index may be stored by the content-addressable file system (e.g., in different IPFS nodes). In this way, a third party (e.g., a doctor, a nurse, a researcher using a patient's medical data) may rapidly identify all transactions involving a patient's medical data to which they are a party.

As described above, all transactions involving a patient's data may be recorded in information (e.g., a file) accessible to the patient. For example, the information may be encrypted based on a private key associated with the patient identifying address. Thus, the transactions may not be directly linkable to a patient. Advantageously, and as an example, the technical scheme described herein may be utilized without the patient being required to take any special actions. For example, medical professionals may create and share medical information with other medical professionals (e.g., based on verbal or written authorization of a patient). At a later point in time, the patient may prefer to gain control over his/her medical information. Thus, the patient may claim ownership of their patient identifying address. Without being constrained by theory, an oracle, smart contract, or system, may be utilized, and ownership of the patient identifying address may be granted to the patient based on satisfaction of particular constraints. For example, the patient may be required to prove his/her identity in various ways, and upon satisfaction of the proof the oracle or smart contract may automatically grant the patient access.

As will be described, a particular oracle may be associated with authentication of users (e.g., patients). For example, the particular oracle may integrate with authentication schemes such as biometric authentication. As another example, the particular oracle may integrate with authentication services, such as based on electronic medical record (EMR) software suites. In this way, the particular oracle may enable a patient to claim ownership of a patient master index.

Advantageously, and as will be described, there may be a multitude of oracles associated with the techniques described herein. For example, a first oracle may enable transactions to be placed on a blockchain network. In this example, the first oracle may update a patient master index as described above. As another example, a second oracle may be used to validate a source of data being used. For example, an EMR or electronic health record (EHR) may be used to store medical data. In this example, the EMR or EHR may be validated. As another example, a third oracle may be used to ensure security. In this example, the third oracle may ensure that other oracles are working properly. For example, the third oracle may assign reputation scores to other oracles. If their performance (e.g., latency) degrades below a threshold, the third oracle may reduce respective reputation scores. Additionally, the security oracle may reduce a reputation score of an oracle associated with a particular data source. As will be described, data sources may integrate with specific oracles. In this way, information (e.g., medical data) may be obtained from the data sources and associate with transactions on a blockchain network. The third oracle may thus assign reputation scores to these oracles. The third oracle may disfavor certain of these oracles, thus reducing or eliminating a data source's ability to use the blockchain network. As another example, a fourth oracle may be associated with a data exchange. In this example, the fourth oracle may enable transfer of information for value. A user may specify settings in a smart contract and/or patient master index regarding medical data they are allowing to be transferred and/or value of the medical data. As another example, a fifth oracle may be associated with compliance. For example, HIPAA release management may be ensured. While these oracles are identified as being separate, it may be appreciated that the functionality provided by these oracles may be combined or further separated. Thus, these oracles may be decentralized and enable complex functionality with respect to the blockchain network. Additionally, each of the oracles described may comprise a multitude of nodes or oracles which may come to a consensus. For example, each oracle may access a patient master index as replicated in different storage locations. In this example, each oracle may then determine something, such as whether an entity is authorized to receive medical information, or decryption of an event. The information determined from each oracle may then be aggregated, and a consensus may be reached. Thus, if a particular one of the oracles reaches a different outcome (e.g., an entity is authorized) then this oracle's conclusion may be discarded in favor of the other oracles (e.g., the entity may not be authorized). Thus, each oracle may have a duplicate node on other hardware or system checking a source (e.g., a patient master index or healthcare master index).

Accordingly, in various embodiments, large amounts of data are automatically and dynamically calculated interactively in response to user inputs, and the calculated data can be efficiently and compactly presented to a user by the system. Thus, in some embodiments, the user interfaces described herein are more efficient as compared to previous user interfaces in which data is not dynamically updated and compactly and efficiently presented to the user in response to interactive inputs.

Further, as described herein, the system may be configured and/or designed to generate user interface data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

Additional embodiments of the disclosure are described below in reference to the appended claims, which may serve as an additional summary of the disclosure.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above and/or below-described embodiments (including one or more aspects of the appended claims).

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

DETAILED DESCRIPTION

Figure 1:
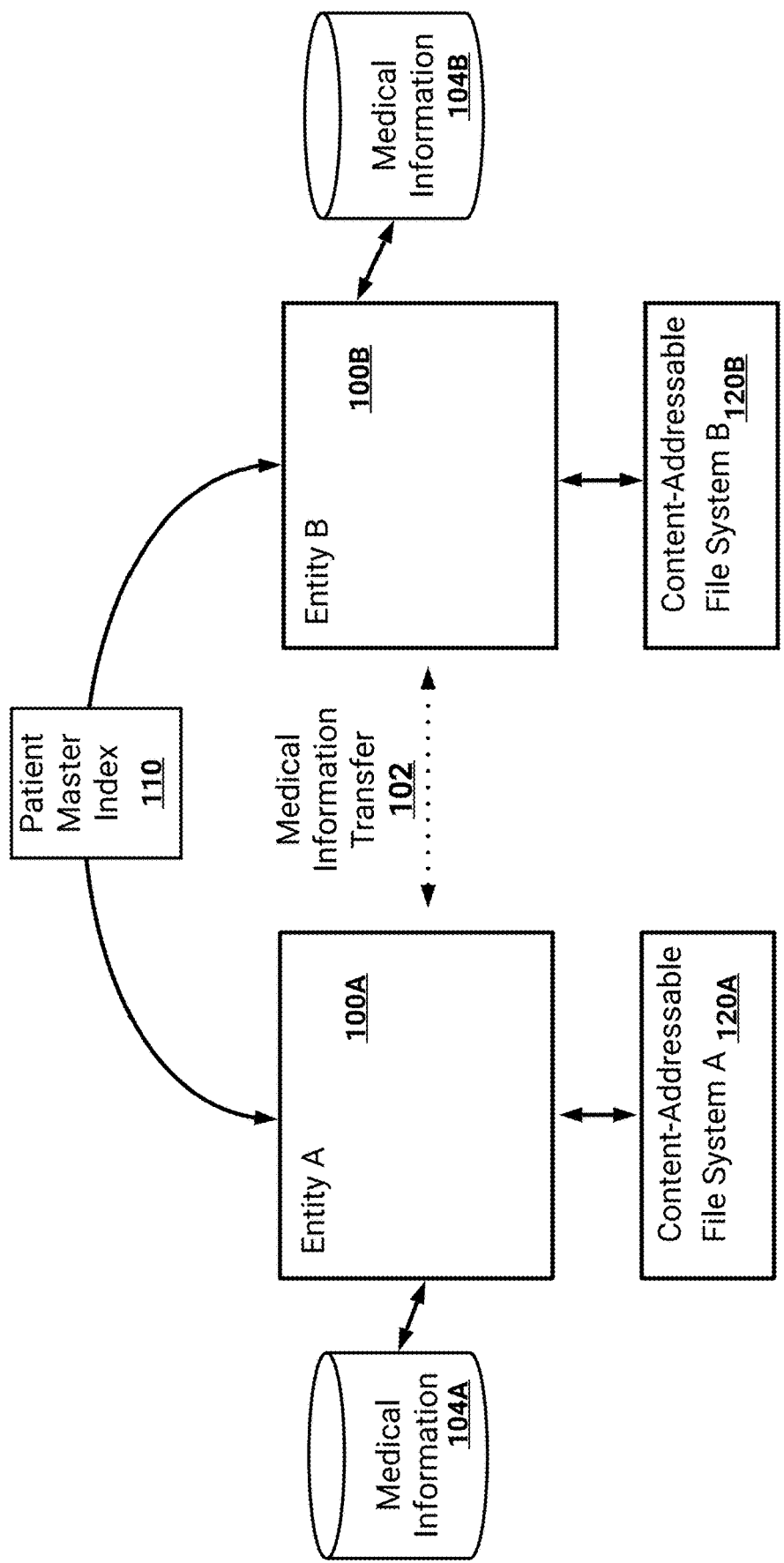
FIG. 1 illustrates an example block diagram for sharing medical information based on a patient master index.

This specification describes a patient centric, and patient controlled, approach to managing access to medical information of the patient. As will be described in more detail below, the approach utilizes a patient master index to ensure that access to medical information is rigidly safeguarded according to a patient's preferences. Additionally, and as an optional example, the patient master index can leverage several levels or types of encryption to ensure that access to the patient master index is only possible by the patient. The patient master index, as described herein, records information indicative of all events that involve the patient's medical information. For example, an event may be a digital request for medical information from a first entity to a second entity. In this example, a doctor may request medical information from another doctor or the patient. As another example, an event may be a medical event. In this example, a patient may visit a doctor's office and the doctor may update or create medical information for the patient. Additionally, the patient master index can identify access permissions to medical information of the patient. For example, the access permissions can indicate that a particular entity is authorized to access particular, or all, medical information of the patient. As will be described in FIGS. 5A-5B, a patient may utilize a user interface to specify access rights, cause sharing of medical information, request his/her medical information, and so on.

The events recorded in the patient master index may be events recorded in a blockchain network. It should be appreciated that transactions recorded in a blockchain network may be publicly accessible, and attempts to adjust recorded information may be impossible. Each transaction in the blockchain network may therefore record, for posterity, all events involving a patient's medical information. As will be described in more detail, each entity may be associated with a unique blockchain address. For example, a patient may have a particular blockchain address referred to herein as a patient identifying address. As another example, a hospital, payor, doctor, and so on, may each have a particular blockchain address. Each blockchain transaction may therefore indicate a sending entity, a receiving entity, and an event.

Since the event may be publicly accessible in the blockchain network, as will be described the event may be a unique identifier associated with medical information being transmitted, shared, and so on. As an example, a first entity (e.g., a first doctor) may request specific medical information from a second entity (e.g., a second doctor). In this example, the first entity may utilize an application, or other software, to specify the requested medical information. A blockchain transaction may then be initiated, with the event being associated with the requested medical information. In this way, a viewer of the blockchain network may be unable to identify the entities at issue in the transaction and the medical information being requested.

As described above, the patient master index can record each event involving a patient's medical information. Thus, and with respect to the example above between the first entity and second entity, the patient master index can be updated to reflect the event. For example, an oracle, or other trusted software, may update the patient master index to record the event. The recorded event may be encrypted, such that only specific entities may view information identifying the requested medical information. As an example, the first entity may be authorized to decrypt the event. As another example, the second entity may be authorized to decrypt the event. Additionally, the patient can decrypt the event. The event may therefore be encrypted based on the public keys associated with the first entity, second entity, patient, and so on. In some embodiments, the smart contract may enable access to the patient master index. Thus, and with respect to some embodiments, the description below regarding decryption of an event included in a patient master index may be understood to represent a smart contract and/or oracle causing decryption of the event. For example, the smart contract may cause private keys to be obtained and used to decrypt the event. The decrypted information may then be provided to a receiving entity.

Optionally, to increase security and further mask information specified in a blockchain transaction, each transaction may utilize a unique transaction address. With respect to the example above, the blockchain transaction may indicate a unique transaction address as the sending entity, and the public address of the first entity as the receiving entity. As another example, a patient may authorize a doctor to access particular medical information. Without use of a unique transaction address, an entity may be able to improperly determine that the patient is transmitting information to the doctor. For example, if the entity improperly determines their respective public addresses. Thus, a unique transaction address may be utilized. In this example, a blockchain transaction may indicate the unique transaction address as the sending address, and a public address of the doctor as the receiving address. While reference is made herein to unique transaction addresses for each blockchain transaction, it should be understood that unique transaction addresses may be utilized for both the sending address and receiving address.

Each blockchain transaction may therefore indicate a unique transaction address. To correlate these unique transaction addresses, a patient transaction index may record all unique transaction addresses associated with a patient's medical information. Access to the patient transaction index may only be provided to the patient, for example the index may be encrypted based on the patient's blockchain address. For events recorded in the patient master index, access to any event may require two or more private keys. Access to an event, as an example, may represent access to medical data associated with the event. For the above-described example involving a patient and his/her doctor, the doctor may be required to have access to a private key associated with his/her blockchain address and a private key associated with the unique transaction address. For example, the private key may be provided (e.g., via an oracle) to a device, application, or other information, utilized or accessible by the doctor. As another example, a smart contract may cause the private key to be obtained. The smart contract may cause the private key to be used to decrypt the event. This decrypted information may then be provided to the doctor (e.g., to a user device of the doctor). In this way, the doctor may decrypt the event and obtain information identifying the particular medical information.

Thus, the patient master index may securely record information identifying all uses of, accesses to, and/or sharing of, medical information of a patient. As described above, the patient may further identify access rights to entities. The access rights may be similarly recorded in the patient master index. Thus, a patient may specify that a particular doctor can access his/her medical information. If the doctor makes an access attempt, an application utilized to access medical information may confirm that the patient master index indicates authorization. Additionally, authorization may be revoked by a patient. For example, a patient may share medical information with an entity. This sharing of medical information will, as described above, be recorded in the patient master index. However, the patient may subsequently revoke authorization to view the shared medical information. If the entity attempts to access the previously shared medical information, an application utilized to access the medical information will identify the revocation of authorization and block access.

Medical information of patients may optionally be stored using a content-addressable file system. For example, the interplanetary file system (IPFS) may be utilized to store information. It should be appreciated that IPFS enables information to be shared via a content address (e.g., a hash). IPFS further enables particular slices or sheets of information as it existed at specific times to be shared. Furthermore, all accesses to information, any changes to information, and so on, can be recorded. Any tampering with the information may be detected. Thus, a patient's medical information may be stored in a content-addressable file system, with nodes (e.g., IPFS nodes) being located at different locations (e.g., different hospitals).

As described above, events may be recorded in the patient master index. Upon decryption of an event, the event may identify one or more hashes corresponding to a patient's medical information. A decrypting entity may then request the medical information corresponding to the hashes. In this way, a medical professional may access, or cause access of (e.g., via a smart contract and/or oracle), an event and obtain one or more hashes corresponding to medical information.

Additionally, medical information stored according to other example schemes may be shared according to the techniques described herein. For example, medical information may be stored in databases controlled by a certain hospital. A doctor may share medical information using a particular health care standard, such as the Health Level 7 standards. As an example, the doctor may institute a Fast Healthcare Interoperability Resources (FHIR) request. A system or application may parse the FHIR request, and identify medical information being shared. For example, the FHIR request may indicate (e.g., using HL 7 messages) a patient identity. Optionally, the system or application may cause the identified medical information to be stored in the content-addressable file system. In this way, one or more unique hashes may be associated with the medical information as stored in the file system. Optionally, the system or application may cause a header (e.g., a JSON header) to be associated with the medical information that identifies one or more hashes. The hashes may be used as hashes for a content addressable file system. For example, the header may be stored with the medical information in the hospital's databases. In this way, the hospital may maintain their databases while reaping the benefits of the techniques described herein. Based on the patient identity, a blockchain transaction may be created that indicates the event (e.g., the sharing of medical information). As described above, the event may be recorded in the patient's patient master index. For example, the event may be encrypted and upon decryption indicate the one or more hashes corresponding to the medical information.

Optionally, files stored in the content-addressable file system may be encrypted, or otherwise locked, with private keys generated by the blockchain network. For example, a smart contract may manage an oracle that can cause information stored in the content-addressable file system to be decrypted only for specific entities. Optionally, smart contracts may manage the oracles, transactions, and data privileges and may be an interface between entities.

FIG. 1 illustrates an example block diagram for sharing medical information 102 based on a patient master index 110. Two entities 100A-100B are illustrated, with the entities representing entities associated with medical information. For example, an entity 100A may be a patient. As another example, an entity 100A may be a doctor. As another example, an entity 100A may be a hospital. In this example, the hospital may store medical information for multitudes of doctors associated with the hospital. As another example, an entity 100A may be a clinic, a pharmacy, a payor (e.g., an insurance company), and so on. The two entities 100A-100B may therefore utilize the techniques described herein to effectuate transfer of medical information. The entities described in FIG. 1 may use respective user devices, such as laptops, tablets, mobile devices, computing systems, and so on. Thus, the entity 100A may be a user device controlled by a patient. In some embodiments, the entities described in FIG. 1 may be software agents. In these embodiments, the software agents may use machine learning techniques to automate the transfer, or receipt, of medical information.

As will be described, a first entity transferring medical information 102 to a second entity may cause a blockchain transaction to be initiated that records the transfer in a blockchain network. For example, entity A 100A may transfer medical information 102 to entity B 100B. Each entity may utilize one or more applications to request and/or receive medical information. As an example, an application may execute on a user device of an entity (e.g., an 'app' obtained from an electronic application store). As another example, an application may execute as a web application executing on a server. The application may be configured based on a type of the entity utilizing the application. For example, a user interface presented to a patient may include information describing his/her medical information, doctors the patient has visited, hospitals the patient has visited, and so on. As another example, a user interface presented to a doctor or other medical professional may enable the doctor to request specific medical information, enter notes, update medical information (e.g., with images), and so on. Optionally, the patient application may be a separate application than the medical professional application.

To transfer medical information 102, entity A 100A may utilize the application to specify medical information 102 for transfer. As an example, the entity A 100A may specify a name of a patient. The entity A 100A may then indicate a transfer of all medical information of the patient to the entity B 100B. For example, the entity B 100B may be a doctor and the patient may be starting to visit the doctor. As another example, the entity A 100A may specify particular medical information of the patient. For example, the entity B 100B may be a specialist who requires only a subset of the medical information of the patient.

A blockchain transaction may then be generated, for example by a smart contract or oracle (e.g., executing on a system of one or more processors, such as included in a public or private cloud) in response to entity A's 100A indication of the transfer. As described above, the blockchain transaction can indicate an event, which in the example herein is the transfer of medical information 102 to entity B 100B. Additionally, a patient master index 110 can be updated (e.g., by an oracle or smart contract) to reflect the event. In some embodiments, a smart contract or oracle may access the patient master index 110 associated with a specified patient. As an example, if entity A 100A is the patient then the smart contract or oracle may authorize the transfer. As another example, if entity A 100A is a doctor then the smart contract or oracle may validate whether the doctor is authorized to transmit the medical information. For example, the patient master index 110 may reflect authorized entities, and the smart contract or oracle may ensure that the doctor is referenced. The event may be a unique hash or string of characters, which can be recorded in the blockchain transaction and patient master index 110. In the patient master index 110, the event may be utilized as a reference to the medical information 102 being transferred. For example, the patient master index 110 may be encrypted (e.g., by a smart contract or oracle), such that only entities involved in events may access the patient master index 110. To decrypt the patient master index 110, private keys associated with the entities blockchain addresses may be utilized. However, an entity involved in an event may only decrypt information for which they have a need to know. That is, the entity may only decrypt events that involve the entity. Upon decryption, information identifying the transferred medical information 102 may be obtained.

In the example of FIG. 1, the blockchain transaction can indicate a public address associated with entity B 100B. Additionally, and as described above, the blockchain transaction can indicate the event. The blockchain transaction may further indicate a unique transaction address, which is specific for the blockchain transaction. For example, this unique transaction address may represent a tumbling public address that is linked to a patient whose medical information 102 is being transferred. The unique transaction address may be recorded in the patient master index 110 (e.g., by an oracle or smart contract). Additionally, the event recorded in the patient master index 110 may be encrypted based on a private key associated with the unique transaction address. The event may also be encrypted based on a private key associated with entity B 100B and/or entity A 100A. The event may also be encrypted based on a private key associated with the patient (e.g., as referred to herein, a private key associated with a patient identity address). To decrypt the event, an entity may be required to have access to two or more of the private keys. For example, the patient may utilize private keys associated with his/her patient identity address and the unique transaction address. As another example, entity B 100B may utilize private keys associated with the unique transaction address and their public address. In some embodiments, an oracle or smart contract may be used to effectuate transfer of these private keys. For example, entity B 100B may receive the private key associated with the unique transaction address. As another example, an oracle or smart contract may use the private keys to decrypt the event, and then cause the decrypted information to be routed to the entity B 100B.

In some embodiments, entity A 100A and entity B 100B may be medical professionals. In this example, the patient master index 110 may specify access rights which are validated to cause the transfer of medical information 102. For example, and as will be described in FIGS. 4A-4B, the patient master index 110 can identify entities authorized to access a patient's medical information. Thus, an oracle or smart contract may cause access to the patient master index 110 and identify whether entity A 100A is authorized to transfer the medical information 102 and/or whether entity B 100B is authorized to receive the medical information 102. Upon a positive identification, the blockchain transaction described above may be initiated.

As described above, the event included in the blockchain transaction can be associated with the medical information 102 being transferred. For example, entity A 100A can identify particular files, images, notes, and so on to be transferred to entity B 100B. The identified medical information 102 may then be ingested, for example by a system of one or more processors. The system may execute, for example, at a hospital, doctor's office, on a server system (e.g., a cloud network), and may access the identified medical information 102. The medical information 102 may then converted into a format addressable by the content addressable file system. For example, unique hashes may be generated and associated with the medical information 102. These unique hashes may be obtained by entity B 100B (e.g., upon decryption of the event, as described above). Thus, the event may encrypt the unique hashes corresponding to the medical information 102. The corresponding medical information 102 may then be obtained (e.g., from a particular node of the content-addressable file system).

As illustrated in FIG. 1, entity A 100A may have access to a database 104A that stores medical information associated with patients. To transfer the medical information 102 to entity B 100B, the specified medical information 102 may be ingested (e.g., as described above). For example, a FHIR request or HL7 message may be generated, and the medical information may be obtained from database 104A. The medical information 102 may then be stored as information in the content-addressable file system (e.g., file system A 120A). In this way, unique hashes corresponding to the medical information 102 may be obtained. The unique hashes may then be recorded in the patient master index 110. These unique hashes may be obtained by entity B 100B based on decryption of the event as described above. Optionally, a hash corresponding to the medical information 102 may be generated as a combination from one or more of the unique transaction address, the patient's address (e.g., patient identity address), public address corresponding to entity A, and/or public address corresponding to entity B. Optionally, the private keys may be utilized in the combination. The combination may generate a hash, such as a cryptographic hash.

Optionally, an oracle or smart contract may maintain mappings to a hash corresponding to the medical information 102 as stored in the content-addressable file system. For example, a first blockchain transaction may include an event corresponding to a transfer of particular medical information. A first hash may be generated from public addresses and/or private keys as described above, and may be recorded in a patient master index. Subsequently, a second blockchain transaction may include an event corresponding to a transfer of the same particular medical information. A second hash may similarly be generated from public addresses and/or private keys as described above. Since this hash may be different (e.g., the entities involved may be different), an oracle or smart contract may maintain mappings from the first hash and second hash to a hash of the particular medical information as stored in the content-addressable file system. The smart contract or oracle may be pinged, or otherwise contacted, and may cause the particular medical information to be provided to the receiving entity.

Optionally, an entity associated with providing medical care, providing payment, and so on, (e.g., an entity that is not a patient) may have their own provider master index. The provider master index may record all events the providing entity is associated with. Additionally, the provider master index may record private keys associated with unique transactions addresses (e.g., as described above). In this way, the provider may have a record of their transactions. The provider may also utilize the private keys to decrypt events as recorded in the patient master index.

Flowcharts

Figure 2:
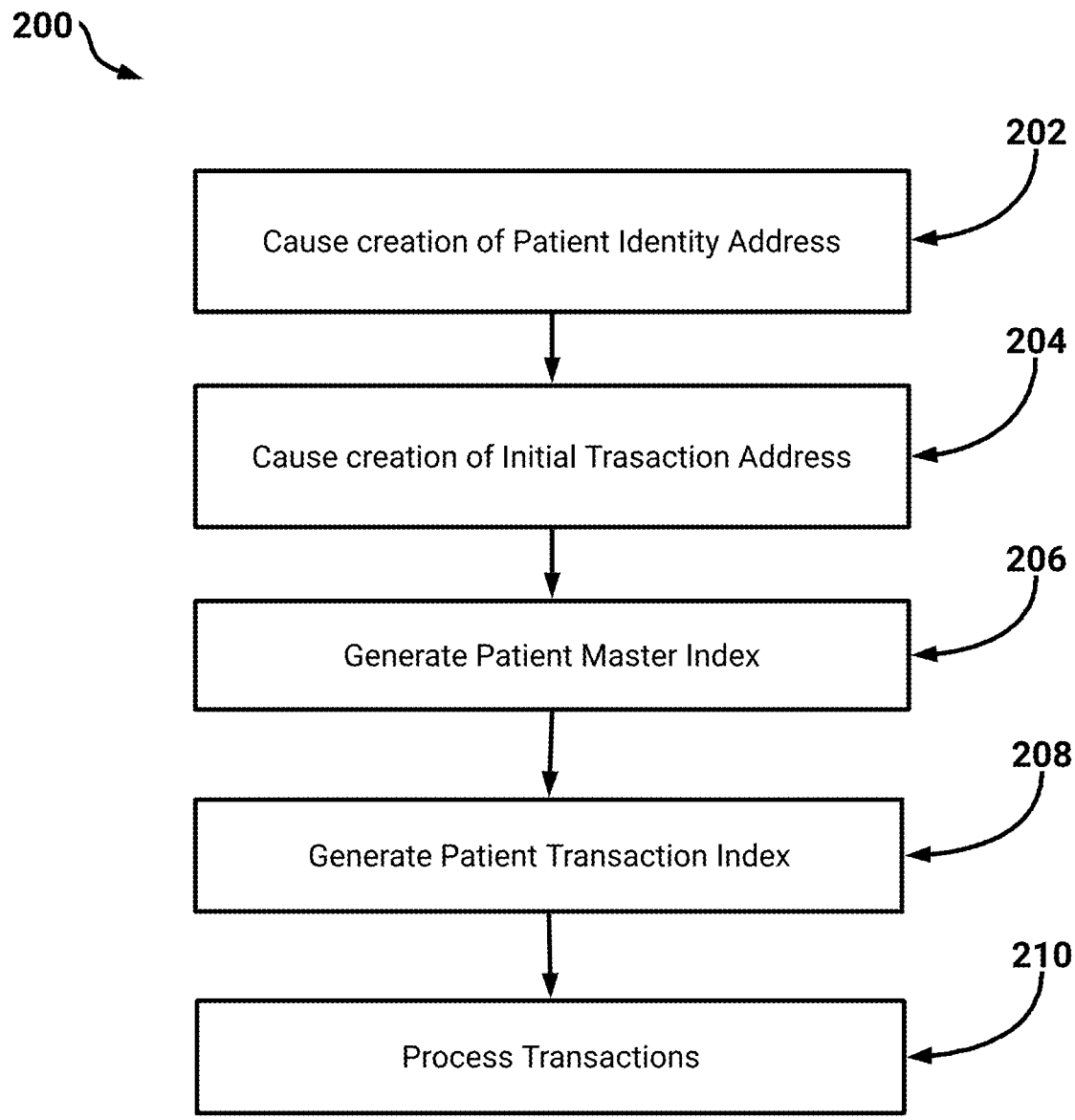
FIG. 2 is a flowchart of an example process for enabling processing of medical information transactions.

FIG. 2 is a flowchart of an example process 200 for enabling processing of medical information transactions. The process 200 may be implemented, at least in part, on a user device of a user (e.g., a mobile device of one or more processors). Additionally, one or more blocks of process 200 may be implemented utilizing an oracle or smart contract associated with a blockchain network. The oracle and/or smart contract may execute via a public or private cloud system or a computing system associated with the blockchain network. In some embodiments, the oracles may be associated with secure enclaves on one or more systems. For convenience, the process 200 will be described as being performed by a system of one or more computers.

At block 202, the system causes creation of a patient identity address. A patient may obtain an application, for example from an 'app' store, and execute the application on his/her user device. The application can provide user interface information to the patient to sign up for the patient-centric scheme described herein. For example, the application may represent a healthcare wallet and may be run on the patient's mobile device.

The application may optionally provide one or more questions to the patient to confirm his/her identity. For example, the application may ask information that only the patient may know. Example questions may include, social security number, specific medical questions from their past (e.g., 'when did you break your wrist'?), and so on. With respect to the medical questions, the application may obtain the information from medical information already existent for the patient. As an example, the patient may identify his/her name and social security number, and the application may access medical information corresponding to the patient. If the questions are answered correctly, a blockchain address may be created with the blockchain address representing the patient's identity address. The patient identity address (e.g., the public/private keys corresponding to the blockchain address) may be stored on the patient's user device. Additionally, the patient identity address may be stored on secure memory (e.g., a USB drive, a secure element on the user device, and so on). To create the blockchain address, a smart contract may optionally be utilized that creates the blockchain address based on correct answering of the questions.

At block 204, the system causes creation of a unique transaction address. In addition to the patient identity address, a blockchain address corresponding an initial unique transaction address can be created. As will be described, each transaction involving the patient's medical information may utilize a distinct unique transaction address. The unique transaction addresses may be linked to the patient identity address, for example in a patient transaction index as described below.

At block 206, the system generates a patient master index. As described above, the patient master index can record all transactions involving the patient's medical information. For example, events may be recorded. Additionally, the patient master index can record access rights specified by the patient. The patient master index may further record unique transaction addresses utilized to transfer medical information of the patient.

The patient master index may be stored on the patient's user device. Access to the patient master index may require a password, biometric authentication, and so on. Additionally, the patient master index may be replicated at different storage locations to ensure that a copy of it exists and can be accessed. For example, a content addressable file system (e.g., the interplanetary file system) may be utilized. The patient master index may therefore be stored on the content addressable file system at different nodes. The patient master index may be encrypted based on the blockchain network. For example, the patient master index may be decrypted, at least in part, using a private key associated with each unique transaction address. In this example, a unique transaction address may decrypt events and/or access rights, with the decrypted events being specific to the unique transaction address. Additionally, the patient master index may be decrypted using a private key associated with the patient identity address. Furthermore, an entity involved in a transaction may decrypt a portion of the patient master index (e.g., events the entity is involved in, access rights, and so on).

At block 208, the system generates a patient transaction index. The patient transaction index may record all unique transaction addresses utilized to transfer medical information of the patient. Thus, the tumbling unique transaction addresses may be associated with the patient. This separation, among other things, may enable a patient's medical information to be transferred between entities (e.g., doctors, hospitals), even if the patient has not yet claimed their identity address. For example, as entities (e.g., doctors, hospitals, researchers) use medical information associated with a patient, the patient transaction index may record all of these uses (e.g., transfers, accesses, and so on). As described block 202, the patient may sign up for a healthcare wallet and thus claim a particular patient identity address. Upon claiming, the patient identity address may be associated with the unique transaction addresses. Thus, the patient may then be able to access the patient transaction index and view a record of all uses of his/her medical information.

At block 210, the system processes transactions. As described above, in FIG. 1, and described below, transfer or medical information may be performed utilizing a blockchain network.

Additionally, a smart contract may be set up in case a patient loses his/her user device or loses access to the patient identifying address. As described above, the patient may be required to answer particular questions, and if answered correctly then access may be granted (e.g., private key associated with the address provided to the patient). Optionally, additional smart contracts may be created. For example, if a patient is found unconscious a medical professional may answer particular questions or provide his/her identity. The smart contract may then grant limited or full access to the patient's medical information. For example, an oracle or smart contract may update the patient master index to identify the access. The access in this scenario, and in general, may additionally have time limits provided on it and enforced by the patient master index, oracle and/or smart contract. Optionally, the patient's identity may be granted separately from the patient's medical information.

Figure 3:
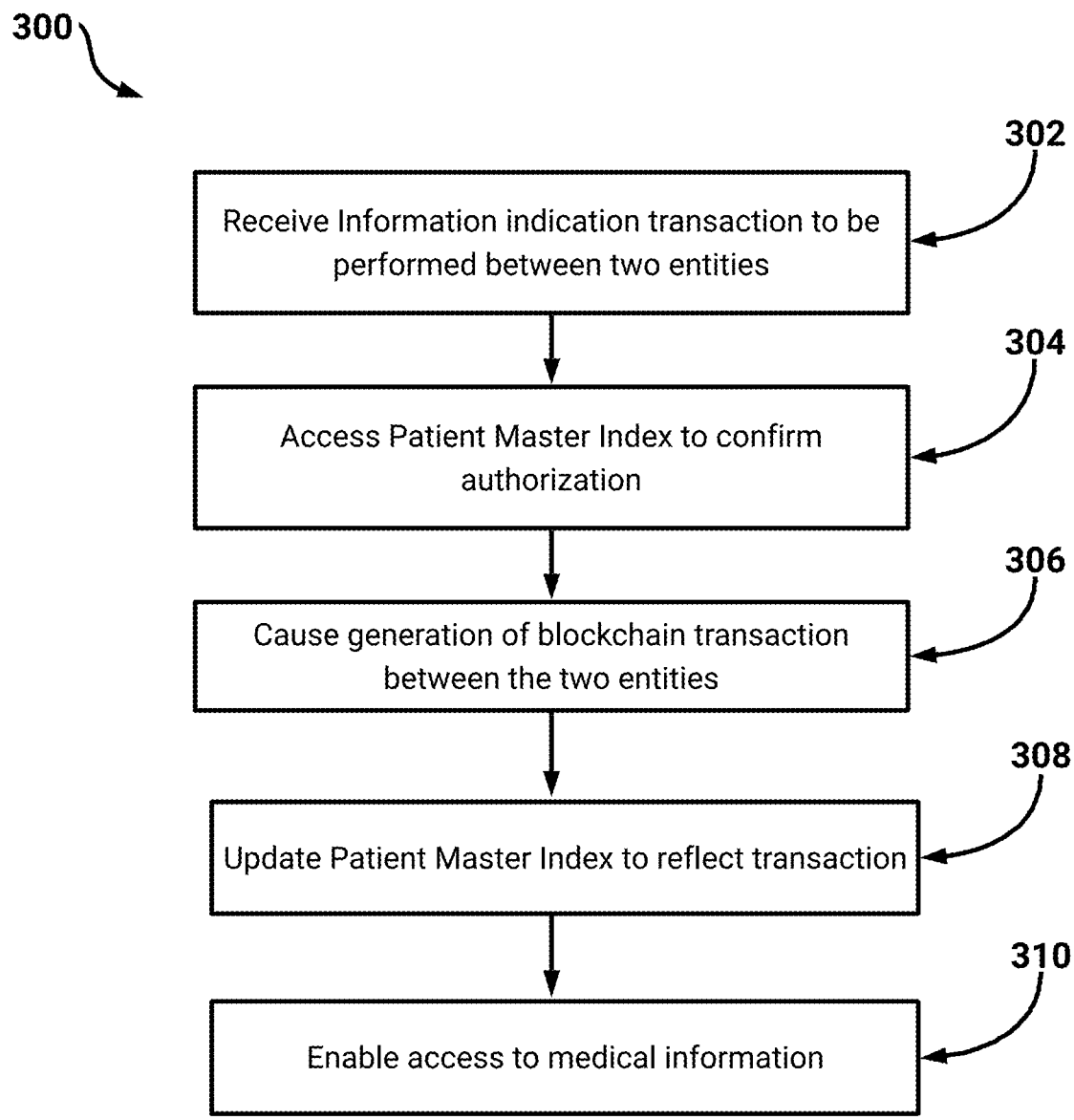
FIG. 3 is a flowchart of an example process for enabling access to medical information based on a patient master index.

FIG. 3 is a flowchart of an example process 300 for enabling access to medical information based on a patient master index. The process 300 may be implemented, at least in part, on a user device of a user (e.g., a mobile device of one or more processors). Additionally, one or more blocks of process 300 may be implemented utilizing an oracle or smart contract associated with a blockchain network. For convenience, the process 300 will be described as being performed by a system of one or more computers.

At block 302, the system receives information indicating a transaction is to be performed between two entities. As described above, an application executing on a user device of an entity may enable requests for medical information associated with a patient to be made. For example, a request may include a request to receive medical information, a request to transfer or share medical information. A transaction may then be triggered based on an event comprising a digital request for information or medical event.

At block 304, the system accesses the patient master index to confirm authorization. The system (e.g., an oracle, smart contract, a device of a requesting entity) may access a patient master index associated with the patient and identify whether the two entities are authorized to perform the transaction.

At block 306, the system causes generation of a blockchain transaction between the two entities. Upon a positive identification of authorization, the system may generate a blockchain transaction identifying an event associated with the transfer or request of medical information. For example, an oracle or smart contract may generate the blockchain transaction. As another example, the system may place a new transaction on the blockchain. Additionally, the blockchain transaction may indicate a unique transaction address and a public address associated with an entity. For example, the public address associated with the entity may be the public address associated with the receiving entity. Furthermore, the unique transaction address may represent a tumbling address associated with the patient.

At block 308, the system updates the patient master index to reflect the transaction. The system (e.g., an oracle or smart contract) may update the patient master index to identify the event included in the blockchain transaction. Additionally, the event may be encrypted such that only the patient and the two entities may decrypt the event. The encrypted event may include the medical information. Thus, upon decryption the medical information may be obtained by the receiving entity. The encrypted event may also identify the medical information, such as a location at which the medical information may be obtained.

At block 310, the system enables access to medical information. The receiving entity may access the patient master index to decrypt the event. In some embodiments, an application executing on the receiving entity's device may notify the receiving entity of the transaction. As an example, the application may monitor transactions on the blockchain. Optionally, the application may be associated with an EHR or EMR system. For example, the application may integrate with the system or maybe be a module included in the system. The application may then access, or cause access of, the patient master index. For example, the application may access the patient master index as stored in a content addressable file system. As another example, an oracle or smart contract may trigger access to the patient master index. In this example, the oracle or smart contract may identify the patient based on the generated unique transaction address. For example, the unique transaction address may be included in a patient transaction index and/or patient master index as described herein. The oracle or smart contract may use private keys associated with the unique transaction address and receiving entity to decrypt the event. The oracle or smart contract may then transmit decrypted information included in the event. Upon decryption, the event can indicate hashes corresponding to medical information associated with the transaction. Additionally, the event can indicate file locations, names of files, and so on, which the receiving entity can access via a request for the files (e.g., from one or more databases or storage systems). For example, the receiving entity can issue a FHIR request. Optionally, the event can include an authentication token, or other authentication information, associated with accessing the medical information.

Example Block Diagrams/User Interfaces

Figure 4A:
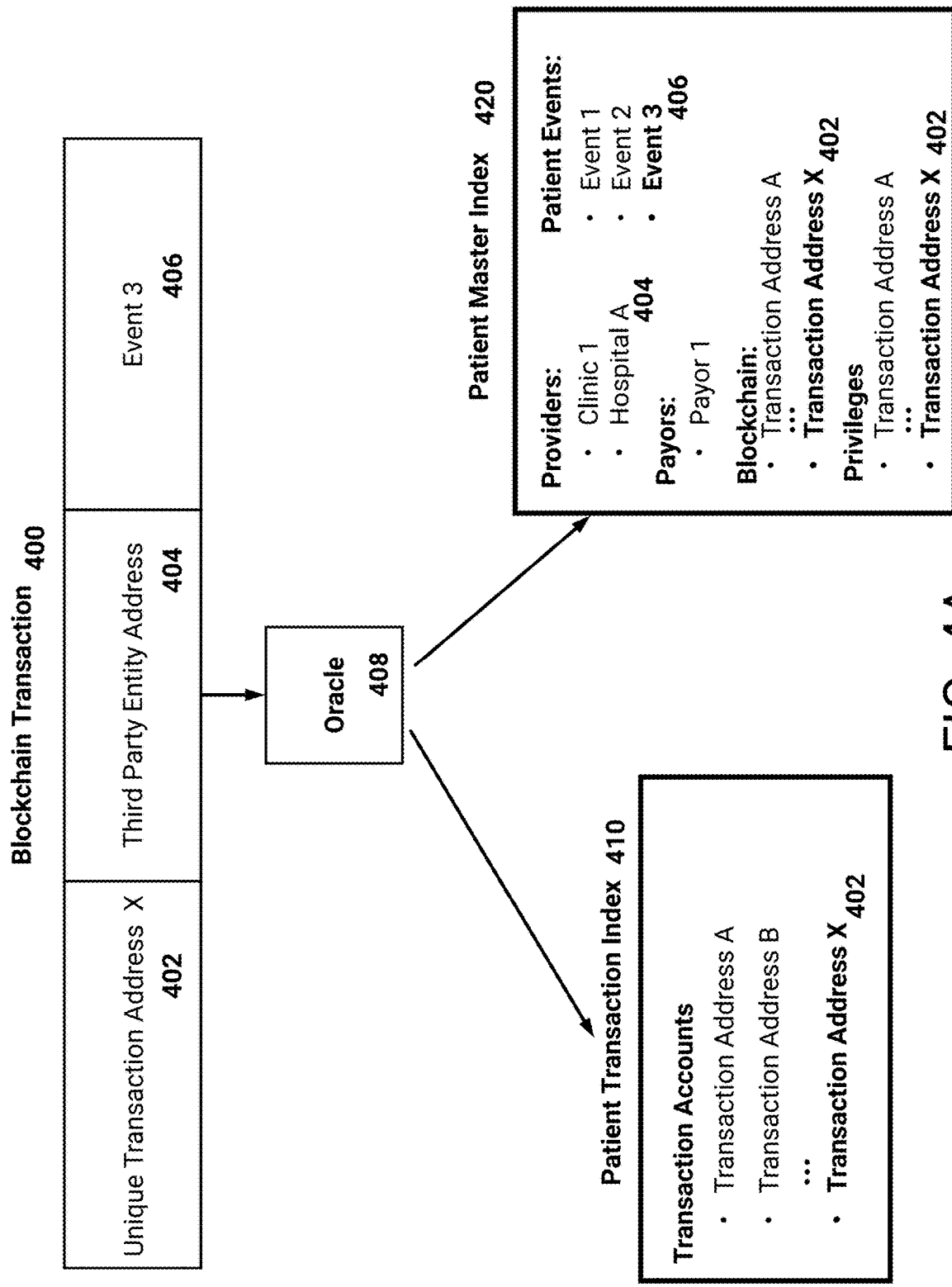
FIGS. 4A-4B are block diagrams of example representations of transferring medical information.
Figure 4B:

FIGS. 4A-4B are block diagrams of example representations associated with transferring medical information. FIG. 4A illustrates an example blockchain transaction 400 that indicates a unique transaction address 402, a third-party entity address 404, and an event 406. This example blockchain transaction 400 may be generated, for example, based on a third-party entity requesting access to particular medical information of a patient. As described above, a unique transaction address for the patient may be generated and included in a blockchain transaction 400. For example, the unique transaction address may be included in a tumbling address associated with the patient. The event 406 may also be created, and may indicate the medical information being transferred. For example, the event 406 may be created to specify a unique hash value associated with a location at which the medical information may be obtained (e.g., from a content addressable file system). The event 406 may additionally represent. Unique identifier associated with a patient master index 420. For example, the unique identifier may correspond to encrypted information included in the index 420

Based on the blockchain transaction 400, an oracle 408 or smart contract or system can update a patient transaction index 410 to reflect the blockchain transaction. For example, unique transaction address X 402 is included in the patient transaction index 410. Additional transaction addresses are reflected in this index 410. These additional transaction addresses relate to transactions involving a patient's medical information. Thus, they may be included in the tumbling address described above, and recorded in the index 410 to record all transactions associated with the patient.

Additionally, the patient master index 420 is updated to record the blockchain transaction 400. As illustrated, transaction address 402 is included in the Blockchain portion of the patient master index 420. This Blockchain portion identifies the unique blockchain addresses utilized in blockchain transactions for the patient. Additionally, transaction address 402 is illustrated in the Privileges portion identifying that the transaction address 402 is authorized for at least one recorded event. Optionally, the third-party entity address 404 may be specified in the Privileges portion.

The event 406 is recorded under the Patient Events portion. As described above, this event 406 may be a unique string or hash value and may be associated with encrypted information. The information may be decrypted by an entity authorized to access the event 406. For example, the third-party entity 404 may decrypt the event 406 based on the entity's 404 private key and optionally a private key associated with the unique transaction address 402. In this example, the third-party entity 404 may use an application or software to enable access to the patient master index 420. As an example, the application may store a location associated with the patient master index 420. As another example, the application may cause an oracle or smart contract to access the patient master index 420. The oracle or smart contract may then validate the third-party entity 404, and cause access to the patient master index 420.

Upon decryption of the event 406, one or more addresses in a content addressable file system may be obtained. These addresses may reflect the medical information being transferred. Thus, the third-party entity may access the content addressable file system and obtain the corresponding information. Optionally, the event 406 may represent a unique identifier associated with encrypted information (e.g., a blob of information). In this example, the third-party entity 404 may cause decryption of the encrypted information. The decrypted information may include medical information, unique hashes associated with a content addressable file system, authentication tokens associated with an EMR or EHR system, and so on.

FIG. 4B illustrates a device 430 of the third-party entity accessing the patient master index 420, and then obtaining medical information from a content-addressable file system 450. For example, the device 430 may utilize the third-party entity's private key and unique transaction address private key to decrypt the event 406 described above. Optionally, the third-party entity may have a provider master index that records, at least, the transactions they are involved in. For example, an oracle or smart contract may update the provider master index. Thus, the third-party entity may obtain a private key associated with the unique transaction address.

The decrypted event 406 may specify identifiers 422 of the medical information being shared. The third-party entity device 430 may utilize the identifiers 434 to obtain medical information 452 from the content addressable file system 450.

Figure 5A:
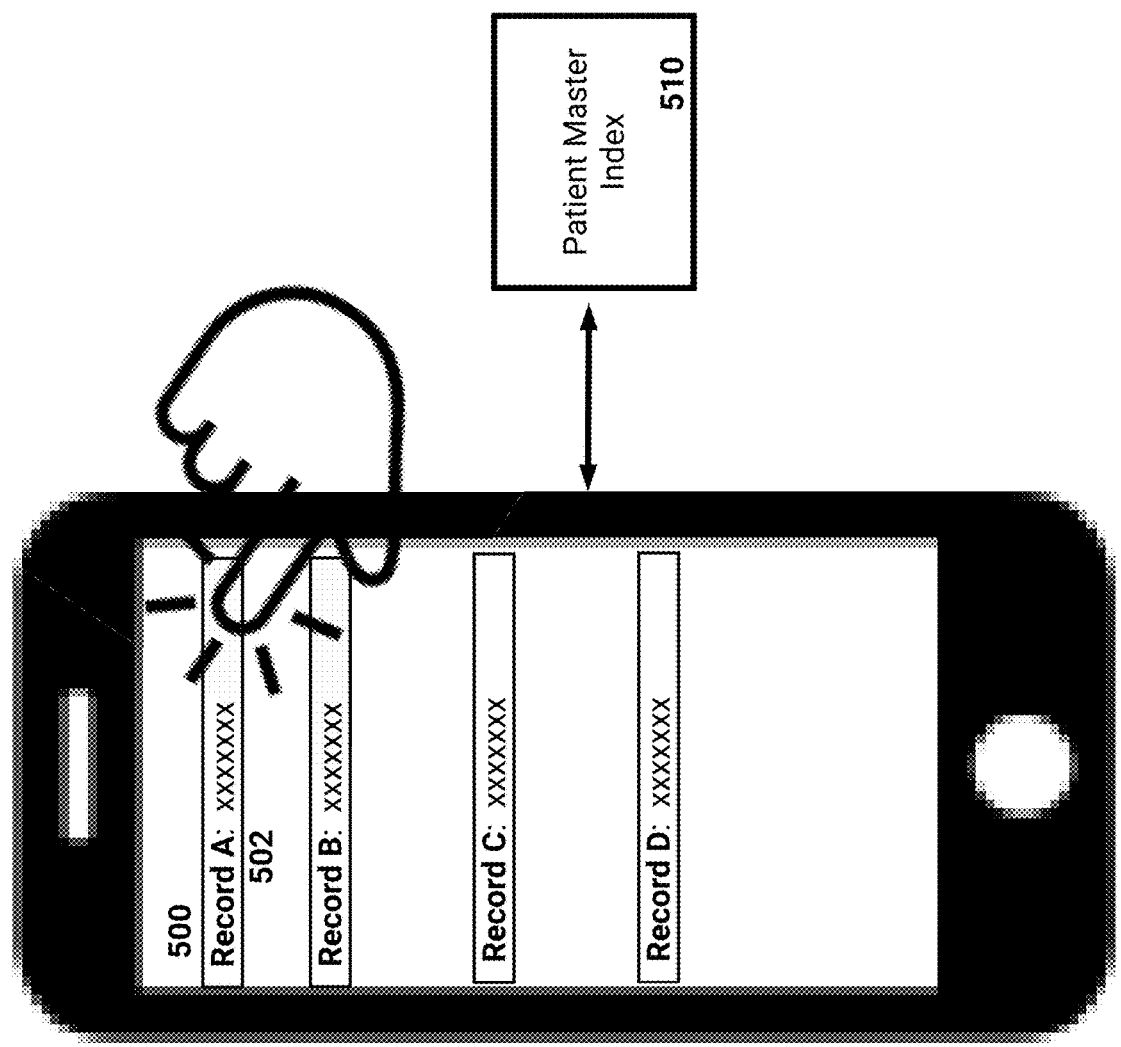
FIGS. 5A-5B are example user interfaces for a patient updating his/her patient master index.
Figure 5B:
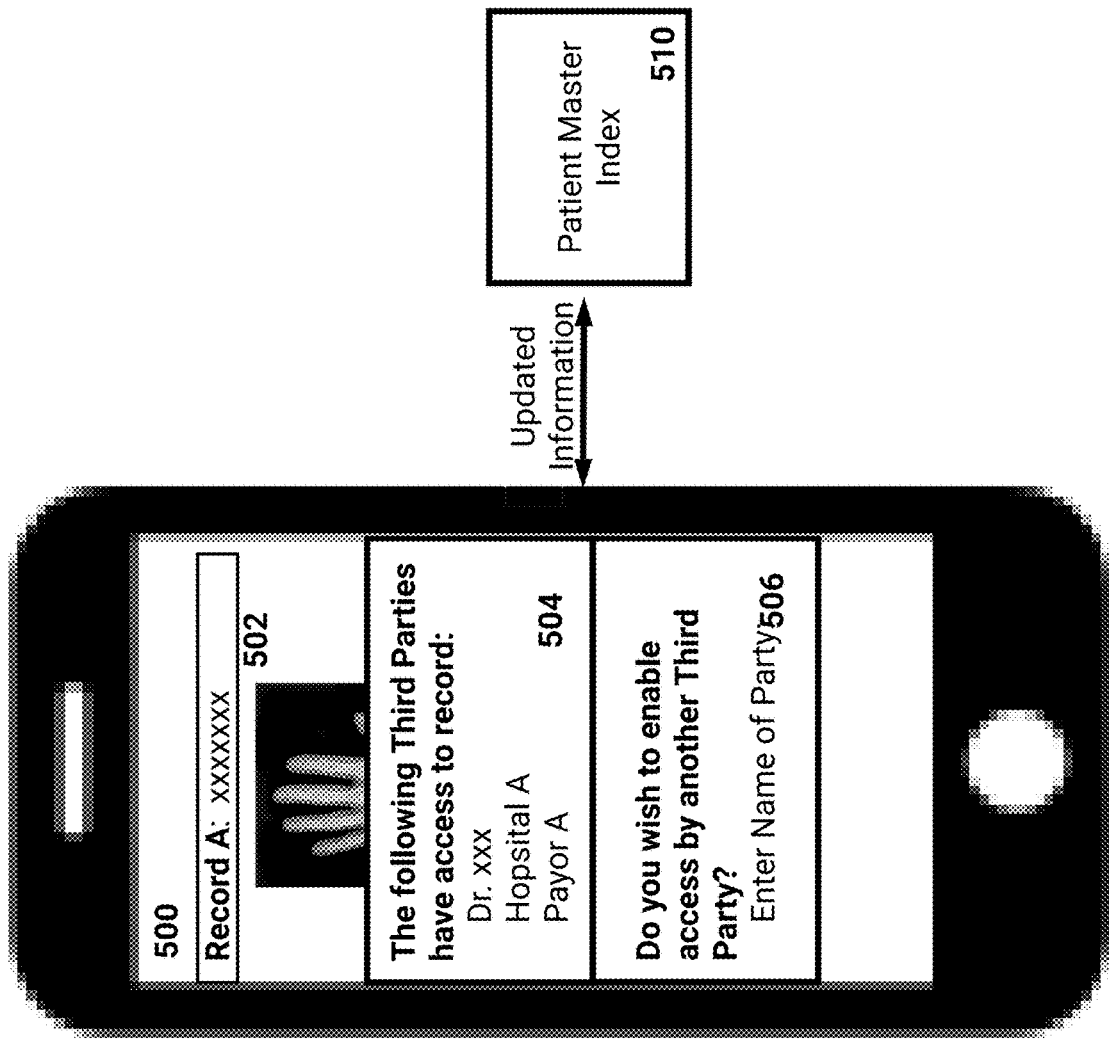

FIGS. 5A-5B are example user interfaces 500 for a patient updating his/her patient master index. As illustrated, the user interface 500 may be presented on a user device of the patient (e.g., a mobile device). The example user interface 500 includes an indication of medical records associated with the patient. For example, Records A-D are illustrated. The user interface 500 may be configured to respond to user input, for example the patient may interact with the presentation of Record A 502 (e.g., select the record 502 on a touch sensitive display). As an example, the patient may press with greater than a particular force or pressure on a display of the user device. As another example, the patient may press for greater than a threshold amount of time on the display of the user device.

Upon interaction, the user interface 500 may update to present information obtained from record A 502. FIG. 5B illustrates the user interface presenting detailed information from the record A 502, including an image (e.g., x-ray) image included in the record A 502.

The user interface 500 further illustrates third parties with access to the particular record A 502 in portion 504. For example, the patient master index 510 may be accessed by the user device and privileges associated with the record may be identified. As an example, the user device may parse the events specified in the patient master index 510 to identify third parties involved in transactions that included the record A 502. Optionally, the privileges portion may specify the access rights. Optionally, the user device may access the content addressable file system to identify actual accesses to the record A 502.

In portion 506, the user interface 500 includes options to enable access by another third party. For example, the patient may specify a name of the third party. An oracle or system may identify a public address associated with the third party, and a blockchain transaction may be generated as described above.

Figure 6:
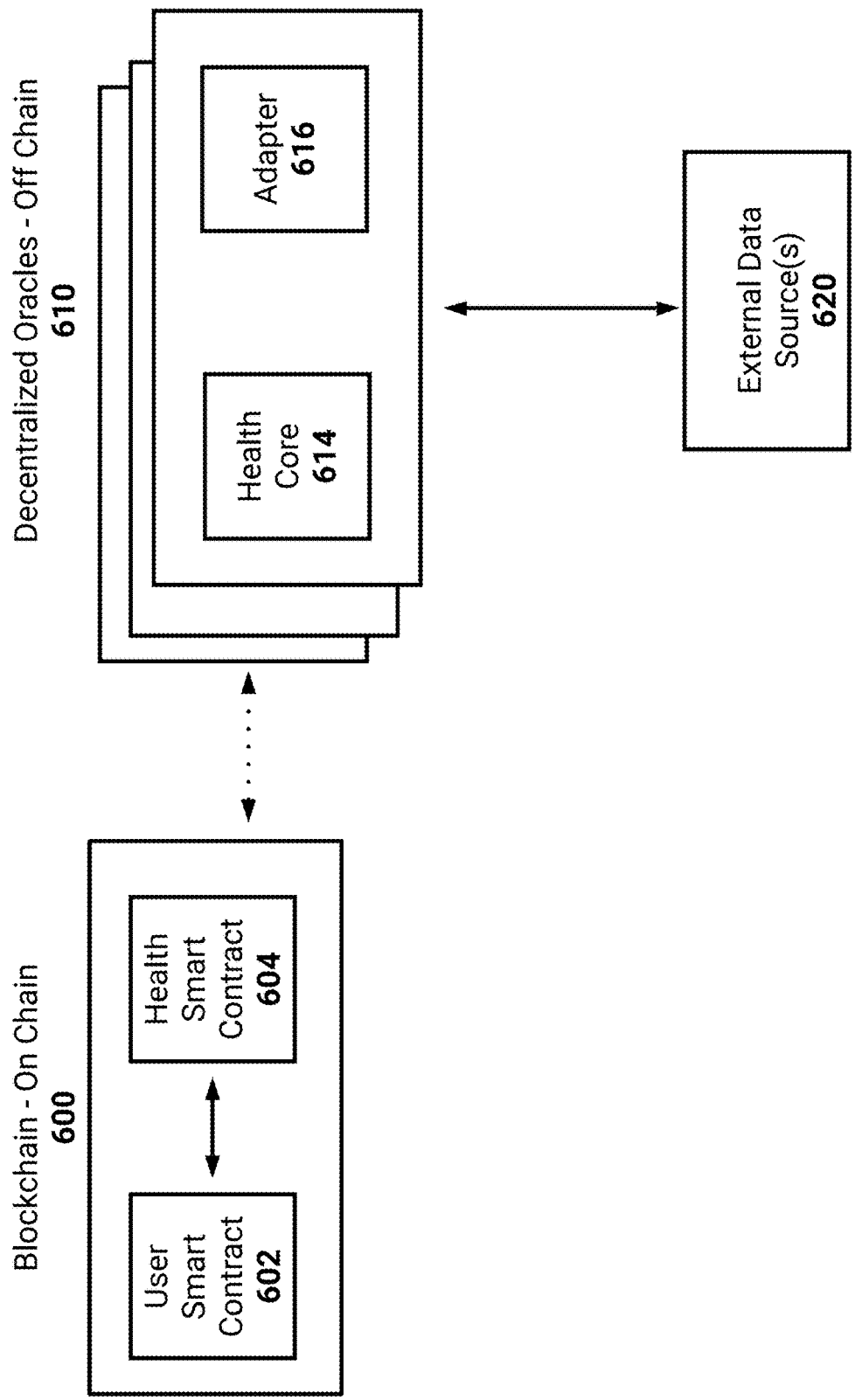
FIG. 6 illustrates an example block diagram of example oracles interacting with a blockchain and external data sources.

FIG. 6 illustrates an example block diagram of example oracles 610 interacting with a blockchain 600 and external data sources 620. As described above, the oracles 610 may execute on a system of one or more computers, such as systems or virtual machines associated with a private or public cloud system. In the description above, an oracle and/or smart contract is described as performing different functionality. In some embodiments, the techniques described herein may leverage multiple decentralized oracles 610 which interact with the blockchain 600.

As illustrated in FIG. 6, a blockchain 600 is illustrated. For example, the blockchain 600 may represent a blockchain network such as Hyperledger as described above. A user smart contract 602 is illustrated as being associated with the blockchain 600. The user smart contract 602 may enable requests to be issued for transference or receipt of medical information. For example, an application executing on a user device of an entity (e.g., as described above) may cause a blockchain transaction to be created. In some embodiments, a user smart contract 602 may enable the creation of the blockchain transaction. As an example, the application may be associated with the user smart contract 602. The user smart contract 602 may receive information, such as the entities involved in a transaction, the medical information to be transferred, privileges to be updated, and so on.

The user smart contract 602 may transmit information to a health smart contract 604. The health smart contract 604 may take a user request, for example transference of medical information, and push the user request to one or more decentralized oracles 610. As will be described, the oracles 610 may then obtain medical information and/or hashes associated with the medical information as stored by a content addressable file system. The oracles 610 may use an example consensus protocol or scheme to ensure that the obtained medical information and/or user request is valid. The health smart contract 604 may then return results, such as any obtained medical information.

As described above, in some embodiments there may be a multitude of decentralized oracles 610. Each of the oracles described below may be replicated and may optionally use different information. For example, the oracles may each determine information and then come to a consensus regarding the determined information. Thus, and with respect to the first oracle described below, a multitude of oracles (e.g., 3, 5, and so on) may access a same patient master index and determine information. This same patient master index may be replicated in different locations, and thus the oracles may ensure that there has been no tampering with either the patient master index and/or the oracles themselves. As an example, a first oracle may cause a patient transaction index and a patient master index to be updated to reflect a transaction. This first oracle may additionally enable the encryption of information, such as in the patient master index. As described above, the encryption may be based on keys associated with blockchain addresses. Thus, this first oracle may safely use keys to enable encryption. The first oracle may then enable decryption of information included in the patient master index. For example, the first oracle may route keys to a receiving entity such that the receiving entity may decrypt an event as described above. As another example, the first oracle may use stored decryption keys to decrypt a portion of the patient master index. The first oracle may then route decrypted information to the receiving entity, for example via the health smart contract 604 as described above.

A second oracle may optionally be used, with the second oracle validating sources of data. For example, the second oracle may ensure functioning of a data source. With respect to an EHR or EMR data source, the second oracle may validate that the data source is able to provide medical information. In some embodiments, the second oracle may identify alternative data sources. For example, there may be a mirror of medical information in a situation in which a data source is not functional. A third oracle may optionally be used, with the third oracle authenticating users. For example, the third oracle may integrate with authentication setups such as setups based on fingerprints, facial recognition, authentication from EHR systems, and so on. In this example, the third oracle may optionally authenticate users prior to allowing the users to access medical information. As described above, a receiving entity may obtain medical information via an event included in a blockchain transaction. In some embodiments, the third oracle may authenticate a receiving entity prior to allowing the third entity to decrypt the event as described herein.

A fourth oracle may optionally be used, with the fourth oracle ensuring security and/or performance of the other oracles. The fourth oracle may assign reputation scores for other oracles and may flag an oracle for a security concern. A fifth oracle may optionally be used, with the fifth oracle enabling a data exchange. For example, a patient may specify that their medical data, or a portion thereof, may be accessed by a researcher for research-based uses. An example of a research-based use is machine learning, as described below. The fifth oracle may therefore receive information from a patient identifying whether the patient prefers to exchange data. This information may be received from the user smart contract 602, for example based on use of an application by the patient. In some embodiments, a sixth oracle may be used. The sixth oracle may optionally ensure compliance, such as HIPAA compliance. The sixth oracle may additionally monitor for alteration of records, such as the right of deletion.

As illustrated, a health core 614 and adapter 616 are included. The health core 614 may interface with the health smart contract 604 described above. The health core 614 may be used to run assignments from the health smart contract 604. For example, the health core 614 may enable the obtaining of medical information from specific data sources (e.g., a specific EMR or EHR system may be associated with a specific health core 614). The adapter 614 may tie into specific data sources and workflows. For example, an adapter 614 may tie into an external data source 620 (e.g., via a rest API). Thus, hospitals may use a unique adapter with their medical data storage schemes.

In some embodiments, the oracles may be associated with reputation scores. It may be appreciated that prior oracles may be capable of being compromised. Thus, the techniques described herein may optionally allow for a multitude of oracles to be associated with the blockchain 600. The oracles may be assigned reputation scores based on how many requests they serviced successfully. For example, a successfully serviced request may indicate successful transference of medical information. The reputation score may also be based on an average time to respond to a request.

Optionally, when an entity wishes to effectuate transfer of medical information the health smart contract 604 may cause oracles to bid on responding. For example, the medical information may be stored at different locations. Thus, different oracles integrated with different external data sources 620 may respond to the health smart contract 604. The health smart contract may aggregate responses and ensure compliance with different service level agreements.

Machine Learning

Patient medical information may be aggregated and utilized to perform machine learning. For example, a patient may indicate in his/her patient master index that his/her medical information may be utilized to perform machine learning. The patient master index may specify particular providers or entities authorized to perform machine learning, and may further identify uses or types of machine learning that can be performed.

The medical information utilized to perform machine learning may be encrypted using homomorphic encryption. For example, an oracle and/or smart contract may cause the homomorphic encryption of medical information. Furthermore, the machine learning model may be similarly homomorphically encrypted. Additionally, the medical information may be supplied from the provider or entity location that is performing the machine learning. As described above, a content addressable file system may be utilized. Thus, the medical information may be automatically mirrored to a node proximate to the provider or a provider's self-maintained node of the file system.

Machine learning models may therefore be utilized and/or trained to gain insights without the medical information being provided in an unencrypted form. Additionally, updated machine learning models (e.g., updated based on homomorphic encryption) may be compared against their prior versions. If they are determined to be more accurate, they may replace the prior versions. Thus, a marketplace for machine learning models may be created. Providers or entities may therefore select machine learning models to be applied to medical information.

Additional Implementation Details and Embodiments

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

As described above, in various embodiments certain functionality may be accessible by a user through a web-based viewer (such as a web browser), or other suitable software program). In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A system comprising one or more computers and non-transitory computer storage media storing instructions that when executed by the one or more computers, cause the computers to perform operations comprising:

receiving information indicating that a transaction is to be performed between two entities, the transaction indicating an event associated with transfer or receipt of medical information associated with a patient;

accessing a patient master index to confirm that the two entities are authorized to transfer or receive the medical information, wherein the patient master index indicates a plurality of events associated with the patient, wherein each event reflects an individual transaction between a transmitting entity and a receiving entity and is associated with an individual address of a blockchain network, wherein the individual addresses form tumbling addresses associated with the patient, wherein a portion of the events is configured to be decrypted by an individual receiving entity based on a private key associated with the individual receiving entity and private keys associated with respective individual addresses of the blockchain network to which the receiving entity was included, wherein a first oracle is configured to transmit the private keys associated with the individual addresses for utilization by the receiving entity in decrypting the portion, wherein the patient master index further includes a portion indicating privileges associated with receiving party access to medical information, wherein the portion identifies unique addresses used in transactions associated with transfer or receipt of medical information associated with the patient, and wherein an individual private key associated with an individual unique address is routed to a particular receiving party enabling decryption of an individual event associated with the unique address;

causing generation of a blockchain transaction between the two entities, wherein an address associated with the blockchain transaction is uniquely generated for the transaction, the address being stored, via the first oracle, in a patient transaction index, wherein the patient transaction index comprises the tumbling addresses associated with the patient, the tumbling addresses being associated with respective transactions, wherein the tumbling addresses include the address associated with the blockchain transaction, and wherein the patient transaction index is accessible only to the patient via a patient private key associated with a patient address;

updating the patient master index to reflect the transaction, wherein the transaction is encrypted using a plurality of public keys associated with at least a subset of: the two entities, the patient, and the address; and enabling access, by a receiving entity of the two entities, to the medical information, wherein the medical information is obtained via the receiving entity using a first private key associated with the receiving entity and a second private key associated with the address provided via the first oracle, wherein a second oracle is configured to validate a source of data associated with the medical information, and wherein a third oracle is configured to assign security scores to the first oracle and second oracle.

2. The system of claim 1, wherein causing generation of a blockchain transaction comprises:

generating an event associated with the medical information, the event comprising a unique identifier; and generating the blockchain transaction comprising the address, the event, and a receiving address associated with the receiving entity.

3. The system of claim 2, wherein generating the blockchain transaction comprises transmitting information to a smart contract, the information reflecting the transaction and the smart contract causing generation of the blockchain transaction.

4. The system of claim 1, wherein updating the patient master index comprises:

storing information identifying an event associated with the medical information, the stored information being encrypted and reflecting locations at which the medical information may be obtained with respect to a content addressable file system.

5. Non-transitory computer storage media storing instructions that when executed by a system of one or more computers, cause the one or more computers to perform operations comprising:

receiving information indicating that a transaction is to be performed between two entities, the transaction indicating an event associated with transfer or receipt of medical information associated with a patient;

accessing a patient master index to confirm that the two entities are authorized to transfer or receive the medical information, wherein the patient master index indicates a plurality of events associated with the patient, wherein each event reflects an individual transaction between a transmitting entity and a receiving entity and is associated with an individual address of a blockchain network, wherein the individual addresses form tumbling addresses associated with the patient, wherein a portion of the events is configured to be decrypted by an individual receiving entity based on a private key associated with the individual receiving entity and private keys associated with respective individual addresses of the blockchain network to which the receiving entity was included, wherein a first oracle is configured to transmit the private keys associated with the individual addresses for utilization by the receiving entity in decrypting the portion, wherein the patient master index further includes a portion indicating privileges associated with receiving party access to medical information, wherein the portion identifies unique addresses used in transactions associated with transfer or receipt of medical information associated with the patient, and wherein an individual private key associated with an individual unique address is routed to a particular receiving party enabling decryption of an individual event associated with the unique address;

causing generation of a blockchain transaction between the two entities, wherein an address associated with the blockchain transaction is uniquely generated for the transaction, the address being stored, via the first oracle, in a patient transaction index, wherein the patient transaction index comprises the tumbling addresses associated with the patient, the tumbling addresses being associated with respective transactions, wherein the tumbling addresses include the address associated with the blockchain transaction, and wherein the patient transaction index is accessible only to the patient via a patient private key associated with a patient address;

updating the patient master index to reflect the transaction, wherein the transaction is encrypted using a plurality of public keys associated with at least a subset of: the two entities, the patient, and the address; and enabling access, by a receiving entity of the two entities, to the medical information, wherein the medical information is obtained via the receiving entity using a first private key associated with the receiving entity and a second private key associated with the address provided via the first oracle, wherein a second oracle is configured to validate a source of data associated with the medical information, and wherein a third oracle is configured to assign security scores to the first oracle and second oracle.

6. The computer storage media of claim 5, wherein causing generation of a blockchain transaction comprises:

generating an event associated with the medical information, the event comprising a unique identifier; and generating the blockchain transaction comprising the unique transaction address, the event, and a receiving address associated with the receiving entity.

7. The computer storage media of claim 6, wherein generating the blockchain transaction comprises transmitting information to a smart contract, the information reflecting the transaction and the smart contract causing generation of the blockchain transaction.

8. The computer storage media of claim 5, wherein updating the patient master index comprises:

storing information identifying an event associated with the medical information, the stored information being encrypted and reflecting locations at which the medical information may be obtained with respect to a content addressable file system.

9. A method comprising:
maintaining a patient master index associated with a patient, the patient master index comprising one or more of:
- identifications of third parties authorized to access medical information associated with the patient,
- unique transaction addresses associated with a blockchain network, the unique transaction addresses indicating blockchain addresses utilized in blockchain transactions to transfer or receive medical information associated with the patient, and the unique transaction addresses forming tumbling addresses associated with the patient,
- identifications of events involving transfer or receipt of medical information associated with the patient, the events being specified in blockchain transactions on the blockchain network,
  - wherein a portion of the events is configured to be decrypted by an individual third party based on a private key associated with the individual third party and private keys associated with respective unique transaction addresses of to which the third party was included, and wherein a first oracle is configured to transmit the private keys associated with the individual addresses for utilization by the third party in decrypting the portion,
  - and wherein the plurality of events are configured to be decrypted by the patient, and
- privileges associated with third party access to medical information wherein the privileges identify unique transaction addresses used in blockchain transactions associated with transfer or receipt of medical information associated with the patient, and wherein an individual private key associated with an individual unique transaction address is routed to a particular third party enabling decryption of an individual event associated with the unique address;

receiving a request from a third party associated with medical information of the patient;

accessing the patient master index, and determining whether the third party is authorized to access the medical information; and upon a positive determination, generating a blockchain transaction indicating an event associated with access to the medical information, wherein a second oracle is configured to validate a source of data associated with the medical information, and wherein a third oracle is configured to assign security scores to the first oracle and second oracle.

10. The method of claim 9, wherein the patient master index is maintained on a user device of a user.

11. The method of claim 9, wherein the patient master index is maintained via a content addressable file system.

12. The method of claim 9, wherein each event is associated with encrypted information indicating medical information associated with the patient.

13. The method of claim 9, wherein the blockchain transaction identifies a unique transaction address and the event associated with the medical information.

14. The method of claim 13, wherein the patient master index is updated to record information associated with the blockchain transaction.

15. The system of claim 1, wherein different portions of the events are configured to be decrypted by respective entities associated with the events, and wherein the plurality of events are configured to be decrypted by the patient.

16. The non-transitory computer storage media of claim 5, wherein different portions of the events are configured to be decrypted by respective entities associated with the events, and wherein the plurality of events are configured to be decrypted by the patient.

17. The method of claim 9, wherein the plurality of events are configured to be decrypted by the patient using a patient transaction index, wherein the patient transaction index comprises the unique transaction addresses, and wherein the events are decrypted using, at least, private keys associated with the unique transaction addresses and a patient private key associated with the patient.

18. The system of claim 1, and wherein based on a security score assigned to the second oracle being below a threshold the third oracle is configured to reduce or eliminate access to the source of data.

19. The system of claim 1, wherein the first oracle is a particular oracle selected from a plurality of first oracles, and wherein the third oracle is configured to disfavor selecting the particular oracle from the first oracles based on its assigned security score being below a threshold.

20. The computer storage media of claim 5, and wherein based on a security score assigned to the second oracle being below a threshold the third oracle is configured to reduce or eliminate access to the source of data.

21. The computer storage media of claim 5, wherein the first oracle is a particular oracle selected from a plurality of first oracles, and wherein the third oracle is configured to disfavor selecting the particular oracle from the first oracles based on its assigned security score being below a threshold.

* * * * *